(12) United States Patent
Maxwell et al.

(10) Patent No.: US 8,342,045 B2
(45) Date of Patent: Jan. 1, 2013

(54) ACTIVITY MONITOR

(75) Inventors: Douglas James Maxwell, Glasgow (GB); Malcolm Howard Granat, Glasgow (GB); Joseph Cyril Barbenel, Glasgow (GB)

(73) Assignee: University of Strathclyde, Glasgow (GB)

( * ) Notice: Subject to any disclaimer, the term of this patent is extended or adjusted under 35 U.S.C. 154(b) by 1738 days.

(21) Appl. No.: 10/471,490

(22) PCT Filed: Mar. 11, 2002

(86) PCT No.: PCT/GB02/01102

§ 371 (c)(1), (2), (4) Date: Jan. 26, 2004

(87) PCT Pub. No.: WO02/071945

PCT Pub. Date: Sep. 19, 2002

(65) Prior Publication Data

US 2004/0112151 A1    Jun. 17, 2004

(30) Foreign Application Priority Data

Mar. 12, 2001    (GB) .................................. 0106037.5

(51) Int. Cl.
*G01L 5/16* (2006.01)

(52) U.S. Cl. ......... 73/865.4; 73/863.21; 33/512; 33/511

(58) Field of Classification Search ................ 73/865.4, 73/863.21; 33/511, 512
See application file for complete search history.

(56) References Cited

U.S. PATENT DOCUMENTS

| | | | |
|---|---|---|---|
| 4,757,453 A * | 7/1988 | Nasiff ........................ 73/379.01 |
| 5,263,491 A | 11/1993 | Thornton | |
| 5,375,610 A * | 12/1994 | LaCourse et al. ............. 600/595 |
| 5,459,676 A * | 10/1995 | Livingston .................... 700/296 |
| 5,941,836 A * | 8/1999 | Friedman ...................... 600/595 |
| 5,955,667 A * | 9/1999 | Fyfe ............................... 73/490 |
| 6,059,576 A | 5/2000 | Brann | |
| 6,122,960 A * | 9/2000 | Hutchings et al. .............. 73/493 |
| 6,129,686 A * | 10/2000 | Friedman ...................... 600/595 |
| 6,165,143 A * | 12/2000 | van Lummel .................. 600/595 |
| 6,301,964 B1 * | 10/2001 | Fyfe et al. ........................ 73/510 |
| 6,513,381 B2 * | 2/2003 | Fyfe et al. ........................ 73/510 |
| 6,611,783 B2 * | 8/2003 | Kelly et al. ..................... 702/150 |
| 6,704,603 B1 * | 3/2004 | Gesotti ........................... 607/62 |

(Continued)

FOREIGN PATENT DOCUMENTS

EP    0 535 508    4/1993

(Continued)

OTHER PUBLICATIONS

U.S. Appl. No. 60/271,090 by Townsend et al., for a Virtual Corset Apparatus, filed Feb. 23, 2001.*

(Continued)

*Primary Examiner* — David A. Rogers
*Assistant Examiner* — Rodney T Frank
(74) *Attorney, Agent, or Firm* — Alston & Bird LLP

(57) ABSTRACT

A method of recording data relating to the posture of a subject and assessing the data so as to categorize said data into activities, including sitting, walking and standing. The method comprises sensing the movement of the thigh by use of a single sensor; recording the movement of the thigh; and processing the data so as to classify the data into discrete ones of said activities.

1 Claim, 3 Drawing Sheets

U.S. PATENT DOCUMENTS

| | | | |
|---|---|---|---|
| 6,834,436 B2 * | 12/2004 | Townsend et al. | 33/512 |
| 6,915,230 B2 * | 7/2005 | Kawai et al. | 702/139 |
| 6,971,267 B2 * | 12/2005 | Kawai et al. | 73/379.01 |
| 7,127,370 B2 * | 10/2006 | Kelly et al. | 702/151 |

FOREIGN PATENT DOCUMENTS

| | | |
|---|---|---|
| EP | 0 943 290 | 9/1999 |
| GB | 2 330 912 A | 5/1999 |
| JP | 06-142087 | 5/1994 |
| JP | 07-178073 | 7/1995 |
| JP | 2000-325329 | 11/2000 |
| WO | WO-81/01507 | 6/1981 |
| WO | WO-96/29007 | 9/1996 |

OTHER PUBLICATIONS

R.M. Glaser, M.R. Heath, C.E. Brubaker and A.B. Wilson, Jr.; *A System for Monitoring Daily Ambulatory Activity*; Proceedings of the Annual Conference of the IEEE/Engineering in Medicine and Biology Society; Nov. 7-10, 1986, ; pp. 579-583; vol. 1, Conf. 8; New York.

International Search Report for PCT/GB02/01102 completed Jun. 24, 2002.

\* cited by examiner

ACTIVITY MONITOR

BACKGROUND OF THE INVENTION

1) Field of the Invention

The present invention relates to monitoring and recording the activity of a subject.

The present invention may be used in a variety of applications that require the assessment of an individual's daily activity in an unconstrained environment. Users of such an apparatus may include health practitioners, who can use the information provided by the device to determine a patient's compliance to a prescribed exercise routine and may further help the patient by motivating them to achieve set targets. Individuals can use the apparatus as a motivational aid to be more active, whilst the apparatus can also be used to provide a convenient means to measure and compare a subject's calorie expenditure with respect to their calorie intake. This device may be further utilized by Clinical Research Organizations who require tools that can provide data to demonstrate the efficacy of new drugs and medical interventions of clinical trials.

2) Description of Related Art

In the healthcare field any intervention associated with a mobility or co-morbidity factor can take advantage of the information given by the device. One such example of where this could be used is to address the issue of the growing evidence of type II diabetes, which can be linked to both obesity and inactivity. Furthermore achieving a general reduction in morbidity is important to the nation as increased ill health is expensive to treat, reduces the work force and decreases quality of life to those affected. This device provides a powerful tool for assessing the impact of mobility and sedentary lifestyles on health.

Devices that measure the activity of a person are well known in the art. Such devices include goniometers which allow continuous measurement of a joint angle, however, the data produced by a single goniometer cannot provide postural information and thus will not be able to assess between the different activities of the user. In addition goniometers are generally not used for long term recordings of unconstrained activities.

Other types of devices available are pedometers which count the number of steps taken in a given period of time and which are normally worn on the waist or ankle. The more sophisticated pedometers make a crude relationship between steps taken and calories used, however, are unable to discriminate between an upright and seated posture and do not record the rate of stepping, only the total number of steps.

Also available are actometers which utilize accelerometers to detect motion, these are similar to pedometers and can be worn on the wrist. These devices may include sophisticated algorithms that infer energy expenditure from the sensor output and most recently such devices have been mounted in the instep of footwear, with claims of the ability to measure the distance and speed of walking and running.

In addition, heart rate monitors are widely used to measure the intensity of exercise performed and while one such monitor presently exists with a calorie function, the calorie function only operates on elevated heart rates over 100 beats per minute, so only estimates the calories used during exercise.

None of the above mentioned devices can provide the data needed to evaluate a number of medical interventions, that is to say, provide results that indicate that the intervention has reduced the persons mobility handicap.

BRIEF SUMMARY OF THE INVENTION

It is amongst the objects of the present invention, to provide an activity profiler that obviates or mitigates one of the aforementioned disadvantages.

According to a first aspect of the present invention there is provided a system for monitoring and recording the activity of a subject, the system comprising a first portable device adapted to be worn by the subject and arranged to record data representative of body position of the subject, and a second device used to assess the data recorded by the first portable device, so as to categorize said recorded data into activities including sitting, standing and walking; said first device comprising:

a single sensing means, adapted to be maintained in a single location about the thigh;

a recording means for storing data from said sensing means;

and a power source to supply both the sensing means and recording means;

said second device comprising a processing means capable of connection to the first device for analyzing and classifying said data into discrete activities.

Thus in use the system can monitor a subject's activity over a period of time, which may be a period of days or weeks, and can classify and quantify said activities into periods spent sitting, standing and walking.

Preferably the sensor is an accelerometer in which a signal is generated that reflects inclination of the thigh.

Preferably the processing means has a set of threshold levels that when applied to the recorded data can be used to distinguish between a seated and an upright posture of the subject.

The threshold levels may be pre-set but, most preferably, the processing means calculates the threshold levels from the recorded data for the particular subject so that the different postures of the subject can be determined.

Preferably the recording means is configured such that it continuously monitors an aspect of the subject's body position.

Conveniently the recording means stores data from the single sensing means at a sampling rate of 10 Hz.

Conveniently the recording means also records the time when the activities are performed by time stamping the recorded data.

Preferably the processing means is programmed to calculate for each activity the total accumulative duration periods.

Conveniently the processing means is programmed such that it can further distinguish the data of the identified walking activity in order to produce information relating to the cadence (rhythm) and total number of steps for said walking activity.

Preferably the processing means is programmed such that it can calculate an estimate of the calorific expenditure of the subject for a specified period.

The recording means and the processing means may be combined to form a single portable module that can be worn by a user. The second device may have a user interface comprising a screen and keys to access information.

Alternatively, the functional process of the processing means is supplied in the form of a computer software package that can be loaded on to a suitable apparatus, such as a personal computer or the like in which case the second device is remote from the first device.

According to a second aspect of the present invention there is provided a method of recording data relating to the posture of a subject and assessing the data so as to categorize said data into activities including sitting, walking and standing, said method comprising:

sensing the movement of the thigh by use of a single sensor;
recording the movement of the thigh; and
processing the data so as to classify the data into discrete ones of said activities.

Preferably the method includes the step of calculating the threshold levels from the data recorded, such that the data can be further processed to determine the primary postures of the subject.

BRIEF DESCRIPTION OF THE SEVERAL VIEWS OF THE DRAWINGS

An embodiment of the present invention will now be described by way of example, with reference to the accompanying drawings, in which:

FIG. 4 is a histogram of occurrence of amplitudes of the sensor output waveform shown in FIG. 3a.

DETAILED DESCRIPTION OF THE INVENTION

Figure 1A:
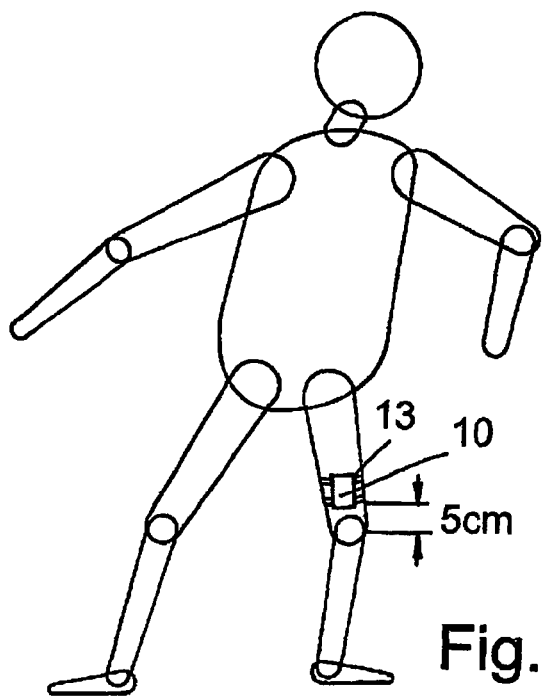
FIG. 1a depicts a first portable device of the system in accordance with the present invention as worn by a user.
Figure 1B:
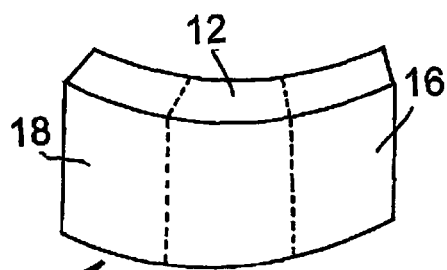
FIG. 1b is a block diagram of the first portable device which includes a sensor.

Referring firstly to FIGS. 1a and 1b, there is shown one embodiment of a system in accordance with the present invention part of which is as worn by a user. The system comprises a first portable device 10 which is maintained in a set location on the thigh of the user, preferably 5 cm above the patella, by means of a strap 13, sticky tape or specially designed pair of body pants (having a specially designed pocket to house the first portable device 10) such that the device 10 remains in constant contact with the thigh and neither rotates around nor slips down the thigh. The first portable device 10 as shown in FIG. 1b, comprises a data logger 16, which is configured to record data representative of body position of the user (or subject) every 1/10th of a second thus achieving a sampling rate of 10 Hz, a sensing means 12 and a power supply 18 to power both the data logger 16 and sensing means 12. The sensing means 12 is preferably a single uni-axial accelerometer which is located mid-line of the thigh, such that the axis of sensitivity of the accelerometer is in the sagittal plane, making it sensitive to the inclination of the thigh.

The first portable device 10 is internally configured such that it transfers power to the sensing means 12 from the power supply 18 and relays a data signal to the data logger 16 from the sensing means 12. Before being stored on the data logger 16, the signal emanating from the sensing means 12 is first pre-filtered using a low pass anti-aliasing filter, so as to remove any unwanted high frequency transients.

Whilst this embodiment illustrates a first portable device 10 formed into a single unit such that it can be worn on the leg of a user, alternative embodiments are also envisaged. The first portable device 10 may be formed such that the sensor 12 is mounted on the thigh and communicates to a data logger 16 and battery 18 located on the waist of the user, for example by means of a cable, or a form of wireless communication.

Figure 2:
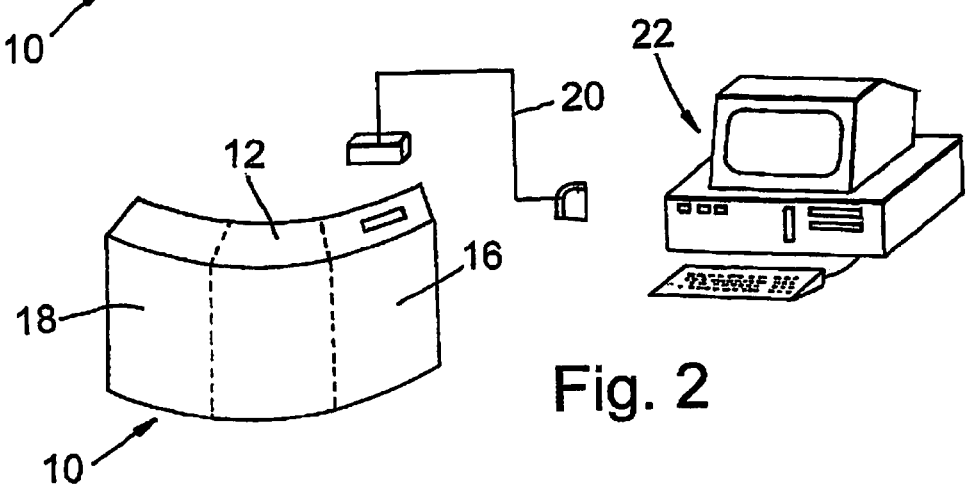
FIG. 2 is a block diagram showing one embodiment of the system in accordance with the present invention.

In FIG. 2 there is shown a second device which takes the form of a processing means 22 connected by way of a data cable 20 to the data logger 16. Once the data has been downloaded to the processing means 22 it is possible to analyze the data by use of specific algorithms to assess the data recorded by device 10 so as to categorize the recorded data into activities including sitting, standing and walking. Whilst in this embodiment data is shown to be transferred between the data logger 16 and processor 22 by a data cable 20, other embodiments of the present invention include wireless means for the transfer of said data.

The steps of the algorithms are to calculate two threshold levels for the acquired data, these threshold levels are then used to categorize the data into representations of upright and seated periods of the user. The identified upright data is then classified into active or quiet periods, in which the active periods are further classified according to speed or vigor. With the data logger 16 configured to record the time of data acquisition it is possible to analyze specific periods of the day, and this data can be used to estimate the calorie expenditure of the subject.

Figure 3A:
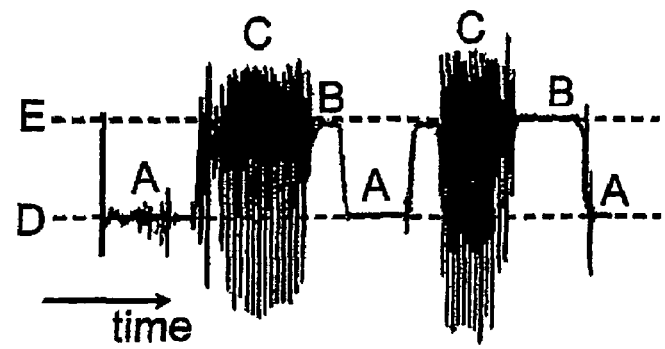
FIG. 3a is a waveform showing different signals typically produced from the output of the sensor of FIG. 1b.

FIG. 3a shows a typical output waveform generated by the sensing means 12, where A represents a period in a seated posture, B represents a period maintained in a standing posture and C represents an upright active period. It can be seen that the signal for the standing posture B is not clearly distinguishable as a discrete value, therefore, the processor 22 is used to computate a discrete dc component E for said standing posture B. In a similar manner a discrete dc component D is also calculated for the seated posture A. The two discrete dc components D, E are defined as the threshold levels and are used to distinguish between the two primary postures, that is to say the seated posture and the upright posture, for the recorded data.

Figure 4:
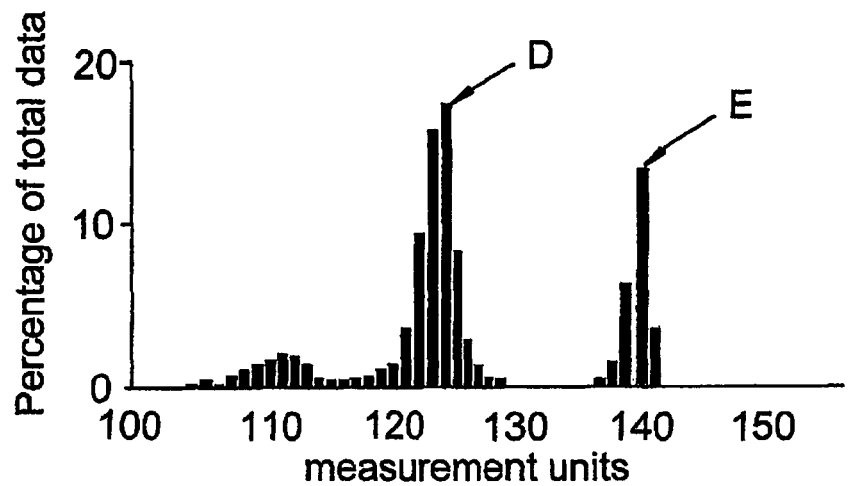

The calculation of the threshold levels D, E is the first operation that is performed once the data has been downloaded into the processing means 22. The method of determining the threshold levels D, E is by manipulating the data as shown in FIG. 4, wherein FIG. 4 shows a histogram of the occurrence of amplitudes of the output of the sensing means 12. From FIG. 4 the processing means 22 determines the most frequently occurring amplitudes around the seated and upright postures, and these values are used as the threshold levels. In FIG. 4 the data shown on the histogram between 120 and 130 on the horizontal axis, which represents the thigh in a horizontal position, indicates the occurrence of amplitudes of the output signal of the sensing means 12 for a subject in a seated position and the most frequently occurring amplitude D would be used as the threshold level for the seated posture. Similarly the data shown around 140 on the horizontal axis, which represents the thigh in a substantially vertical position, indicates the occurrence of amplitudes of the output signal of the sensing means 12 for a subject standing or walking and the peak amplitude E would be used for the threshold level for the standing posture.

Figure 3B:
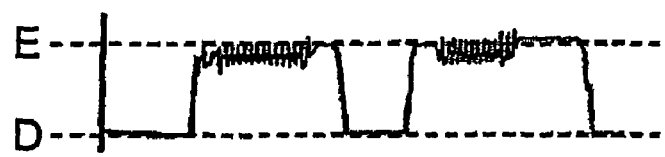
FIG. 3b shows the waveform of FIG. 3a after being passed through a low pass filter.

Once the threshold levels D, E have been calculated, the second step is to classify the entire data record into upright and seated postures according to the calculated threshold levels D, E. This step is performed by first passing the signal of FIG. 3a through a low pass filter, of around 10 Hz, so as to produce a waveform as shown in FIG. 3b to remove the high frequency oscillations, and noise, caused by heel-striking of the user during walking, as represented at C in FIG. 3a. This filtered signal is then classified into periods of upright and seated postures by use of the threshold levels, D, E. The classification process can be performed by several methods including the use of comparators, band stop filters or the like. This process step allows the processing means 22 to classify the data such that it can determine and calculate the total accumulative periods for the seated and upright periods and is further used as a mask to identify the upright periods so that these upright periods can be further classified.

The third operation that is performed is to separate the identified upright posture classification into active and quiet periods. This is achieved by using the results obtained in the second step as a mask to process the original unfiltered signal of FIG. 3a, so as to obtain the upright periods from the original signal.

Figure 3C:
FIG. 3c shows the waveform of FIG. 3b after being rectified about a threshold.
Figure 3D:
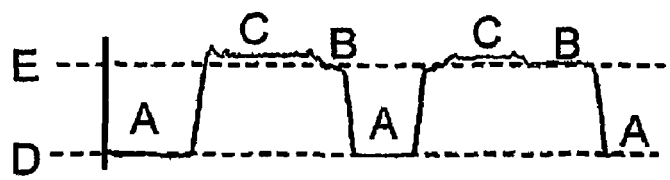
FIG. 3d shows the waveform of FIG. 3c after being passed through a low pass filter to identify a walking period.

The previously identified upright portions of the filtered signal, that is to say the signal located around E as shown in FIG. 3b are then rectified about the upright threshold level E, so that the identified upright activity located below the threshold level E is reflected above E. (Alternatively, this step can be performed by calculating the differential between the active period of the signal lying below the threshold E and adding the modulus of these differential values to E.) This results in the waveform as shown in FIG. 3c, where all the upright activity is represented by a signal above the threshold level E. The rectified signal is then low pass filtered using a moving average filter, to remove the oscillations as shown in FIG. 3d, and to produce an envelope C which corresponds to a discrete average signal for the walking period.

Thus, the oscillating signals represented by C in FIG. 3a corresponding to walking, have been converted into a signal with a value greater than that of the upright threshold value E; the standing posture has a value equal to that of the threshold level E; and the sitting or lying position has a value equal to D. Transitions between standing and sitting are represented in the waveform by those transitions between the threshold levels D, E. The data as displayed in FIG. 3d can now be categorize according to three activities, sitting/lying A, standing B and walking C.

Figure 5:
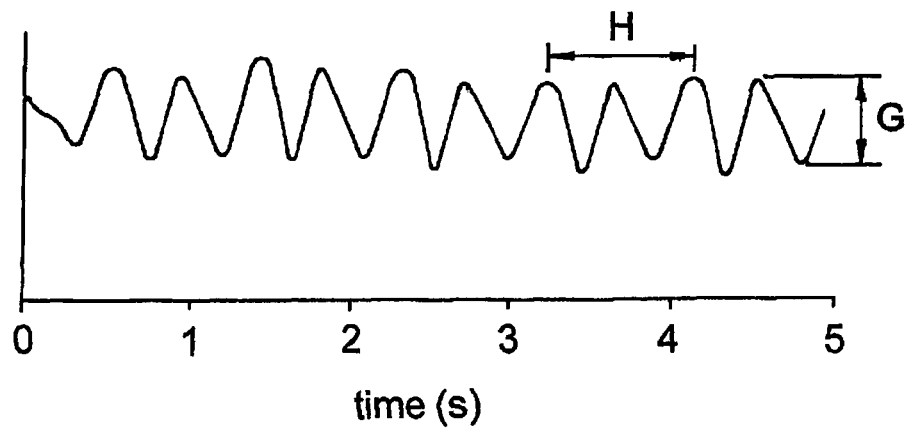
FIG. 5 shows a time-expanded portion of the FIG. 3c waveform.

The data of the identified walking period as processed and shown in FIG. 3b can be further analyze. FIG. 5 displays a portion of this data with an expanded timescale to allow the individual steps of the subject user to be visualized. Referring to FIG. 5 a single step is represented by the occurrence of a double oscillation from one peak in the waveform to the second following peak, that is to say from a crest to the second following crest of the signal along the timescale, i.e. a step is as shown by H in FIG. 5. By analyzing this data the cadence (rhythm) and total number of steps can be calculated. The higher the frequency of the signal, that is to say the closer together the peaks are along the time scale, the faster the rhythm of the upright activity, which may be walking or indeed running. Conversely, the lower the frequency, or the further apart the peaks are along the time scale, the lower is the pace or rhythm. Furthermore the excursions of the signal during each step can be analyzed to discriminate the activity even further, that is to say the peak to peak amplitude G of a step is measured to classify the signal between walking and other high stepping activities, such as running or cycling, as during high stepping activities the higher inclinations of the thigh creates a larger peak-to-peak amplitude G generated by the sensing means 12.

Therefore, from the process steps taken by the processing means 22, to classify the recorded data into different activities, it is possible to determine an individual's activity during a normal day. The processor 22 can also calculate the amount of time spent performing different activities such as standing, walking and sitting and to estimate the calorie burn or energy expenditure of the subject by multiplying the time spent in each activity by an index of energy expenditure. The index of energy expenditure can be derived from published work and incorporates factors relating to the subject's height, weight and fitness. Separate values would be attributed to sitting, standing and walking. The walking value would be scaled according to the published values relating walking cadence with energy expenditure.

The invention claimed is:

1. A system for recording and processing data relating to the activities of a subject, the system comprising:
    an accelerometer adapted to be maintained in a single location about a thigh of a subject and operable to generate inclination and motion sensitive data that reflects the inclination and motion of the thigh;
    recording means for recording the inclination and motion sensitive data from the accelerometer; and
    a processor for processing the recorded inclination and motion sensitive data so as to classify activities into discrete ones of sitting, walking and standing activities, based on the inclination and motion sensitive data, wherein the processor is programmed to calculate an estimate of the calorific expenditure of the subject for a specified period.

* * * * *